United States Patent [19]

Komori et al.

[11] Patent Number: 4,839,162

[45] Date of Patent: Jun. 13, 1989

[54] COSMETIC

[75] Inventors: Takashi Komori; Masahiko Asahi, both of Tokyo; Toshiyuki Suzuki, Ichikawa, all of Japan

[73] Assignee: Kao Corporation, Tokyo, Japan

[21] Appl. No.: 135,038

[22] Filed: Dec. 18, 1987

[30] Foreign Application Priority Data

Jan. 28, 1987 [JP] Japan .................. 62-18042

[51] Int. Cl.$^4$ .............................. A61K 7/021
[52] U.S. Cl. ...................... 424/63; 424/69; 424/401; 514/506
[58] Field of Search ............ 424/69, 63, 401; 514/506

[56] References Cited

U.S. PATENT DOCUMENTS

| | | | |
|---|---|---|---|
| 3,592,940 | 7/1971 | Quesada | 424/69 |
| 3,963,649 | 6/1976 | Spadini et al. | 252/546 |
| 4,056,113 | 11/1977 | Johnson et al. | 252/545 |
| 4,104,403 | 8/1978 | Barker et al. | 514/784 |
| 4,440,665 | 4/1984 | Mather et al. | 252/356 |
| 4,528,283 | 7/1985 | Lang et al. | 514/844 |

FOREIGN PATENT DOCUMENTS

| | | |
|---|---|---|
| 526376 | 7/1979 | Australia . |
| 0153857 | 9/1985 | European Pat. Off. . |
| 0164894 | 12/1985 | European Pat. Off. . |
| 0704687 | 2/1954 | United Kingdom . |
| 2013235 | 3/1970 | United Kingdom . |
| 1375639 | 11/1974 | United Kingdom . |
| 1458798 | 12/1976 | United Kingdom . |
| 1538032 | 1/1979 | United Kingdom . |
| 2021141 | 11/1979 | United Kingdom . |
| 2166149 | 4/1986 | United Kingdom . |

Primary Examiner—Ellis P. Robinson
Assistant Examiner—P. J. Ryan
Attorney, Agent, or Firm—Oblon, Spivak, McClelland, Maier & Neustadt

[57] ABSTRACT

Cosmetic comprising a diglyceride which is liquid at room temperature, and a polyol type humectant. It may take any form such as an oily cosmetic, emulsion cosmetic, aqueous cosmetic and can suitably be applied to roughened skin, or hair requiring a humectant effect. They can provide a high, long-lasting moisturizing effect, and at the same time preserve the moisturizing function of the skin or hair after a lapse of time or even after the portion to which it was applied has been washed. These effects are further promoted by formulating to the cosmetics a specific type hydrophilic humectant.

3 Claims, No Drawings

COSMETIC

BACKGROUND OF THE INVENTION

1. Field of the Invention

This invention relates to a cosmetic and, more particularly, to a cosmetic having a high, long-lasting moisturizing effect.

2. Description of the Background

A normal horny layer of epidermis usually contains 10-20% of moisture which helps to impart elasticity, flexibility, or softness to the skin and to maintain a protective effect for the skin. It is known that when the moisture content decreases to less than 10% due to changes in environmental conditions or the like, this will cause the skin to lose its elasticity and protective function and develop a so-called dry-skin condition which causes various skin problems.

In order to avoid the dry-skin condition or to recover normal skin conditions, a hydrophilic humectant is included in the formulation of cosmetics. Hydrophilic humectants conventionally used are polyol compounds, such as polyethylene glycol, polypropylene glycol, dipropylene glycol, propylene glycol, and butylene glycol, glycerine, sorbitol, maltitol, amino acid, sodium pyrrolidone carboxylate, urea, lactic acid, hyaluronic acid, collagen, and the like.

However, these humectants are too hydrophilic to penetrate the horny layer of the normal skin. They usually remain on the surface of the epidermis, giving only an inadequate and temporary moisturizing effect to the skin.

In view of this situation the inventors have made extensive and earnest studies to obtain a cosmetic with a high and long-lasting moisturizing effect, and found that when both a diglyceride which is liquid at room temperature, and a polyol type humectant are included in the formulation of a cosmetic, they exhibit a moisturizing effect which is higher than when they are ued independently. In addition, it was found that the persistency of the effect can be synergetically enhanced. Such findings have led to the completion of this invention.

SUMMARY OF THE INVENTION

Accordingly, an object of this invention is to provide a cosmetic comprising (A) a diglyceride which is liquid at room temperature and (B) a polyol type humectant component which is freely soluble in the component (A) at room temperature.

DETAILED DESCRIPTION OF THE INVENTION AND PREFERRED EMBODIMENTS

The component (A) used in this invention is a diglyceride which is liquid at room temperature, and has a melting point of not more than 20° C. Such components may be prepared by separating or purifying a glycerine ester of a fatty acid containing more than 60% of diester, which is obtained by esterification of glycerine fatty acid, by glycerolysis of animal or vegetable oils and fats of natural origin, or by glycerolysis of a higher fatty acid-higher alchohol ester, by means of molecular distillation, solvent extraction, and the like. Among them particularly preferable compounds are di(2-ethylhexanoic acid) glycerine ester, dioctanoic acid glycerine ester, and dioleic acid glycerine ester. The component (A), the diglyceride, is formulated in a cosmetic in an amount of 1-50% by weight, preferably 5-25% by weight.

It is essential that the polyol type humectant, the component (B), can mix with the component (A) at an arbitrary proportion at room temperature. This components (B) may be polyethylene glycol, polypropylene glycol, dipropylene glycol, propylene glycol, butylene glycol, hydroxypropyletherized-glycolipid ester (PSL), or the like. Taking the compatibility with the component (C), a hydrophilic humectant, into account, especially preferred compounds are dipropylene glycol and butylene glycol. In addition, a PSL represented by the following formula can be preferably used.

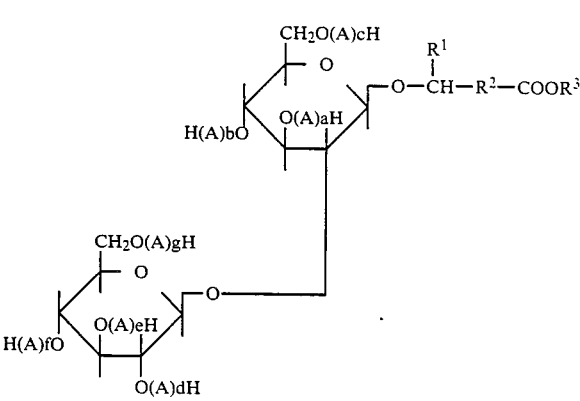

in which $R^1$ is $C_3$ or H, $R^2$ represents a saturated or unsaturated hydrocarbon group having 11-15 carbon atoms when $R^1$ is $CH_3$ and a saturated or unsaturated hydrocarbon group having 12-16 carbon atoms when $R^1$ is H, A represents

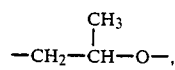

$R^3$ represents a saturated or unsaturated hydrocarbon group having 1-20 carbon atoms or $(A)_hH$, and a, b, c, d, e, f, g, and h are integers the total of which is 1-60. The component (B), the polyol type humectant, is formulated to a cosmetic in an amount of 2-90% by weight, preferably 5-50% by weight. If the amount is less than 2% by weight, the effect of this invention can not be exhibited. On the other hand, when the amount exceeds 90% by weight, the effect proportional to the used amount can no longer be realized. Although there is no specific limitation to the proportion of the components (A) and (B) in a cosmetic, a ratio of (A)/(B) in the neighborhood of 1/2 is preferable.

The component (C), a hydrophilic humectant, used in this invention includes natural humectants such as glycerine, sorbitol, maltitol, amino acid, sodium pyrrolidone carboxylate, urea and lactic acid, as well as hyaluronic acid, chemically modified collagens, and the like. These hydrophilic humectants may be formulated in a cosmetic of this invention in the amount of 2-25%. The hydrophilic humectants preferably have a solubility of not less than 10% by weight in component (B) at room temperature.

In addition to the above essential components, the cosmetic according to the present invention may be formulated as appropriate and to the extent not impairing the effect of the invention with various components which are generally used in cosmetics. These other components may include a surface active agent, humectant other than mentioned above, ultraviolet absorber, chelating agent, pH adjusting agent, preservative, vehicle, coloring agent, perfume, and the like.

The cosmetic according to this invention may take any form such as an oily cosmetic, emulsion cosmetic, aqueous cosmetic, and the like which can suitably be applied to roughened skin, hair, or the like requiring a humectant effect.

The cosmetic of the present invention has a high, long-lasting moisturizing effect. It can preserve the moisturizing function of the skin or hair after a lapse of time or even after the portion to which it was applied has been washed. Thus the cosmetic can exhibit a marked effect for especially maintaining injured or roughened skin or hair in good condition.

Other features of the invention will become apparent in the course of the following description of the exemplary embodiments which are given for illustration of the invention and are not intended to be limiting thereof.

EXAMPLES

Example 1

Mixtures having formulations as shown in Table 1 were prepared and their long-lasting moisturizing effects were measured.

<Formulation>

TABLE 1

| Components | Diglyceride* | Dipropylene glycol | Glycerine | Pure water |
|---|---|---|---|---|
| Comparative Product No. 1 | 100 | — | — | — |
| Comparative Product No. 2 | — | 100 | — | — |
| Comparative Product No. 3 | — | — | 100 | — |
| Comparative Product No. 4 | — | — | — | 100 |
| Comparative Product No. 5 | 50 | — | 50 | — |
| Inventive Product No. 1 | 50 | 50 | — | — |
| Inventive Product No. 2 | 25 | 50 | 25 | — |

*2-ethylhexanoic acid diglyceride

<Test Method>

The above samples were applied to the axilla side of the arm of each subject, left for 1 hour, and then washed off with hot water. The subjects stayed in a room with a constant temperature and humidity of 20° C. and 50%. After 15 minutes, the moisture content of the horny layer was measured by an impedance meter (manufactured by IBS Co.). Two hours later, washing with hot water was repeated, and 15 minutes thereafter the measurement of the moisture content was again conducted. The results are shown in Table 2, in which the moisture contents (unit: $\mu v$) are indicated in mean values (N=10).

<Results>

TABLE 2

| Long-lasting moisturizing effect | 15 min. later | 2 hours later |
|---|---|---|
| Comparative Product No. 1 | 95 | 50 |
| Comparative Product No. 2 | 100 | 50 |
| Comparative Product No. 3 | 115 | 65 |
| Comparative Product No. 4 | 90 | 60 |
| Comparative Product No. 5 | 110 | 60 |
| Inventive Product No. 1 | 135 | 75 |
| Inventive Product No. 2 | 150 | 85 |

As can be seen from Table 2 the Inventive Product No. 1 which is a dipropylene glycol/diglyceride mixed system has a greater moisturizing effect which lasts a longer period of time than those systems which are formulated independently with diglyceride and dipropylene glycol. Thus, it is evident that the two compounds exert their effects synergistically. In addition, the Inventive Product No. 2 shows that addition of the component (C) is also effective.

Example 2

Creams having formulations as shown in Table 3 were prepared and their long-lasting moisturizing effects were measured.

TABLE 3

| | (wt %) | | |
|---|---|---|---|
| Components | Comparative Product No. 6 | Comparative Product No. 7 | Inventive Product No. 3 |
| (1) Petrolatum | 6.0 | 6.0 | 6.0 |
| (2) Cetanol | 3.0 | 3.0 | 3.0 |
| (3) Hydrophobic glycerine monostearate | 2.0 | 2.0 | 2.0 |
| (4) POE (20) sorbitan monoglyceric acid ester* | 2.0 | 2.0 | 2.0 |
| (5) Diglyceride** | — | 19.0 | 19.0 |
| (6) Olive oil | 19.0 | — | — |
| (7) Butyl paraben | 0.1 | 0.1 | 0.1 |
| (8) Methyl paraben | 0.1 | 0.1 | 0.1 |
| (9) Dipropylene glycol | 10.0 | — | 10.0 |
| (10) Perfume | 0.1 | 0.1 | 0.1 |
| (11) Pure water | 57.7 | 67.7 | 57.7 |

*POE (20): polyoxyethylene with 20 moles added oxyethyle groups
**A mixture of 2-ethylhexanoic acid diglyceride (10 parts) and octanoic acid diglyceride (9 parts)

<Method of Preparation>

The oil components (1)–(7) in the above table were mixed, heated to dissolve, and kept at 70° C., to which solution a water phase comprising the components (8)–(11) was gradually added and emulsified by a mixer. The emulsion was cooled to 30° C. by a heat exchanger to obtain a cream (Inventive Product No. 3). The Comparative Products Nos. 6 and 7 were prepared in the same manner.

<Test Method>

A prescribed amount of the above samples were applied to the axilla side of the arm of each subject, left for 2 hours, and then washed off with hot water. The subjects stayed in a room with a constant temperature and humidity of 20° C. and 40%. After 15 minutes, the moisture content of the horny layer was measured by an impedance meter (manufactured by IBS Co.). Washing with hot water and the measurement of the moisture content in the horny layer were repeated at 1, 2 and 5 hours following the initial washing. The results are shown in Table 3, in which the moisture contents (unit: $\mu v$) are indicated in mean values (N=4).

<Results>

TABLE 4

| Long-lasting moisturizing effect | Blank | Comparative Product No. 6 | Comparative Product No. 7 | Inventive Product No. 3 |
| --- | --- | --- | --- | --- |
| Right after initial washing | 32 | 59 | 55 | 87 |
| 1 hour later | 33 | 55 | 50 | 77 |
| 2 hours later | 33 | 48 | 47 | 63 |
| 5 hours later | 31 | 39 | 35 | 51 |

As can be seen from Table 4 the cream according to this invention has a higher moisturizing effect which lasts a longer period of time than those creams which are formulated independently with diglyceride [the component (A)] and dipropylene glycol [the component (B)]. Thus, it is evident that these components exert a synergistic effect in an emulsion system.

Example 3

Milky lotion

<Formulation>

| Oil Phase: | |
| --- | --- |
| Cetanol | 0.5 (%) |
| Petrolatum | 1.0 |
| Octanoic acid diglyceride | 10.0 |
| POE (10) monooleic acid ester | 2.0 |
| Stearic acid | 2.0 |
| Water Phase: | |
| 1,3-butylene glycol | 3.0 |
| Dipropylene glycol | 6.0 |
| Triethanolamine | 1.0 |
| Ethyl paraben | 0.1 |
| Methyl paraben | 0.2 |
| Perfume | 0.1 |
| Pure water | 74.1 |
| | 100.0 |

<Method of Preparation>

Components for the oil phase were mixed, heated to dissolve, and kept at 70° C. Components for the water phase were also mixed and heated to 70° C. Then, the former mixture was added to the latter and emulsified by a mixer. The emulsion thus obtained was cooled to an ultimate temperature of 30° C. by a heat exchanger to obtain a milky lotion.

Example 4

Two-phase lotion

<Formulation>

| Oil Phase: | |
| --- | --- |
| Oleic acid diglyceride | 5.0 (%) |
| POE (20) sorbitan tetraoleic acid ester | 0.2 |
| Ethyl paraben | 0.1 |
| Ethanol | 10.0 |
| Water Phase: | |
| 1,3-butylene glycol | 4.0 |
| Dipropylene glycol | 2.0 |
| Perfume | 0.1 |
| Pure water | 78.6 |
| | 100.0 |

<Method of Preparation>

POE (20) sorbitan tetraoleic acid ester and ethyl paraben were added to oleic acid diglyceride and dissolved. Ethanol was added to this mixture to form the oil phase. The water phase was prepared by adding and dissolving 1,3-butylene glycol, dipropylene glycol and perfume in water. The oil phase was added to the water phase, and the mixture was thoroughly agitated and filtered through a nylon cloth to obtain the final product.

Both cosmetics of this invention as prepared in Examples 3 and 4 exhibited an excellent long-lasting moisturizing effect.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. A moisturizing cosmetic comprising:
   (A) 1–50% by weight of a diglyceride which is liquid at room temperaure and has a melting point of not more than 20° C., and
   (B) 2–90% by weight of a compound selected from the group consisting of polyethylene glycol, polypropylene glycol, dipropylene glycol, propylene glycol, butylene glycol, and hydroxypropyletherizedglycolipid ester.

2. A cosmetic according to claim 1, which further comprises the component (C) which is a hydrophilic humectant having solubility of not less than 10% by weight in the component (B) at room temperature.

3. A cosmetic according to claim 2, in which said component (C) is a compound selected from the group consisting of glycerine, sorbitol, maltitol, amino acid, sodium pyrrolidone carboxylate, urea and lactic acid.

* * * * *